United States Patent [19]

Nielsen

[11] 4,091,040

[45] May 23, 1978

[54] PROCEDURE FOR MAKING TRIMETHYLOLMETHANE

[75] Inventor: Arnold T. Nielsen, China Lake, Calif.

[73] Assignee: The United States of America as represented by the Secretary of the Navy, Washington, D.C.

[21] Appl. No.: 817,752

[22] Filed: Jul. 21, 1977

[51] Int. Cl.² ............................................. C07C 29/14
[52] U.S. Cl. ..................................... 568/853; 260/467; 260/602; 260/615 A; 560/180
[58] Field of Search ........................ 260/635 A, 635 E

[56] References Cited

U.S. PATENT DOCUMENTS

| 2,400,724 | 5/1946 | Walker | 260/635 A |
| 3,076,847 | 2/1963 | Prelog | 260/635 A |
| 3,808,280 | 4/1974 | Merger et al. | 260/635 A |
| 3,912,785 | 10/1975 | Suzuki | 260/635 A |

FOREIGN PATENT DOCUMENTS

| 49-33169 | 5/1974 | Japan | 260/635 A |

OTHER PUBLICATIONS

Breusch et al., "Chem. Berichte," vol. 88, (1955), pp. 1511–1519.

*Primary Examiner*—Joseph E. Evans
*Attorney, Agent, or Firm*—R. S. Sciascia; Roy Miller; L. E. K. Pohl

[57] ABSTRACT

A process for the production of trimethylolmethane in high yields. Trimethylolmethane is useful as the essential precurser to trimethylolmethane trinitrate, a high-energy plasticizer and explosive.

1 Claim, No Drawings

PROCEDURE FOR MAKING TRIMETHYLOLMETHANE

BACKGROUND OF THE INVENTION

1. Field of the Invention

This invention relates to a method for preparing trimethylolmethane.

2. Description of the Prior Art

Trimethylolmethane trinitrate is a high-energy plasticizer and explosive recently developed by Thiokol Corporation. It is thermally more stable and less sensitive than nitroglycerine and, accordingly, could find use as a replacement for nitroglycerine (and other high-energy plasticizers) in certain formulations. Additionally, it is more energetic than trimethylolethane trinitrate. Still further, it is ultimately less costly than bis-(2-fluoro-2,2-dinitroethoxy) methane. However, there is a problem associated with the preparation of trimethylolmethane trinitrate. The problem is the availability of its precurser—trimethylolmethane.

Trimethylolmethane—the essential material from which the nitrate is prepared—is only available via low yield methods. The most reliable published method is that of Breusch and Oguzer. Their method, reported in *Chemishe Berichte*, Vol. 88, pp. 1,511–1519 (1955), produces a yield of only 4–17 percent of the desired compound based on the unrecovered amount of the starting compound, diethyl malonate.

SUMMARY OF THE INVENTION

According to this invention, a method for producing trimethylolmethane in yields of over 50 percent based on the unrecovered amount of the starting compound, diethyl malonate, is provided. The method involves (1) the reaction of diethyl malonate with ethyl orthoformate to produce ethyl ethoxymethylenemalonate; (2) the reaction of ethyl ethoxymethylenemalonate with sodium ethoxide to produce diethyl diethoxymethylmalonate; (3) the reaction of diethyl diethoxymethylmalonate with lithium aluminum hydride to produce 3,3-diethoxy-2-(hydroxymethyl)-1-propanol; (4) the acidification of a solution of the propanol to a pH of 2.5; and (5) the reaction of the unrecovered product produced by acidification with $H_2$ in the presence of a Ru-C catalyst to produce the desired trimethylol methane.

DESCRIPTION OF THE PREFERRED EMBODIMENTS

The chemical reactions involved in the method of this invention may be illustrated by the following equations:

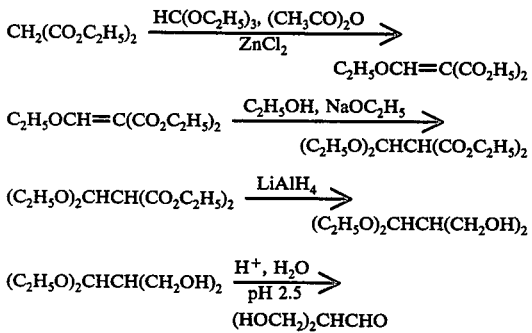

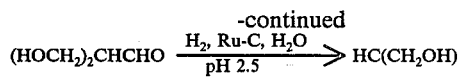

The experimental work conducted in carrying out the five reactions illustrated by the five equations set forth above is described in the following four examples. Example 4 describes both the reaction illustrated by equation 4 and the reaction illustrated by equation 5. The $(HOCH_2)_2CHCHO$ produced by the acidification of 3,3-diethoxy-2-(hydroxymethyl)-1-proponal is not isolated but is merely left in solution and reacted with hydrogen in the presence of ruthenium-charcoal catalyst to produce the desired trimethylolmethane as will be apparent from Example 4.

All of the temperatures in the following examples are in ° C.

EXAMPLE 1

Diethyl Ethoxymethylenemalonate

A mixture of diethyl malonate (160 g., 1.0 mole), ethyl ortho-formate (148 g., 1.0 mole), acetic anhydride solvent (204 g., 2 moles) and anhydrous zinc chloride catalyst (0.5 g) was heated in an oil bath for 6.5 hr (temperature of contents 104°–113° C). The mixture was then distilled through a short column during 3.5 hr, raising the pot temperature to 124°and yielding 120 ml of distillate. The residue was treated with additional ethyl orthoformate (148 g., 1.0 mole) and acetic and acetic anhydride (204 g., 2.0 moles) and distillation was continued for 3 hr to yield 160 ml of distillate (pot temperature 120°–130°). After standing at 25° for 18 hr the residue was diluted with 250 ml of ether and washed thoroughly with water. The combined extracts were dried over magnesium sulfate and distilled to yield a forerun (26 g.) containing principally diethyl malonate and 156 g. (72%) of ethyl ethoxymethylenemalonate, b.p. 109°–111° (0.9mm) (85% yield based on unrecovered diethyl malonate); NMR ($CDCl_3$): $\delta$ 7.62 (s,1,=CH), 4.22 (q. J = 7Hz, 2, $CH_2$), 4.19 (q, J = 7 Hz, 4, $CH_2$), 1.37 (t, J = 7 Hz, 3, $CH_3$), 1.30 (t, J = 7 Hz, 6, $CH_3$).

EXAMPLE 2

Diethyl Diethoxymethyl-malonate

A solution of ethanolic sodium ethoxide (prepared by addition of 0.6 g. of sodium to 60 ml of absolute ethanol) was added slowly, with cooling to diethyl ethoxymethylenemalonate (108 g., 0.5 mole) keeping the temperature of the reaction mixture below 40°. After heating at 35°–40°for 1 hr the solution was adjusted to pH 6.5 by the addition of acetic acid. Distillation gave 109 g. (83%) of diethyl diethoxymethylmalonate, b.p. 101°–103° (0.3 mm); NMR ($CDCl_3$): $\delta$ 5.3, 3,73 (q, 2, J = 8 Hz, CH), 4.22 (q, 4, J = 7 Hz, $CH_2$ of $C_2H_5CO_2$), 3.70 (q, J = 7 Hz, 2, $CH_2$ of $C_2H_5OCH$), 3.67 (q, J. = 7 Hz, 2, $CH_2$ of $C_2H_5OCH$), 1.27 (t, J = 7 Hz, 6, $CH_3$ of $C_2H_5CO_2$), 1.17 (t, J = 7 Hz, 6, $CH_3$ of $C_2H_5OCH$).

EXAMPLE 3

3,3-Diethoxy-2-(hydroxymethyl)-1-propanol

To a solution of 38 g. (1.0 mole) of lithium aluminum hydride in 650 ml of ether (nitrogen atmosphere) was added dropwise, wtih stirring, a solution of 84.2 g. (0.32 mole) of diethyl diethoxymethylamalonate in 100 ml of ether during 2 hr. The mixture was heated under reflux with continued stirring for 23 hr. Ether (200 ml) was added and then water (165 ml) was added very cautiously with stirring during 5 hr. Carbon dioxide was bubbled rapidly into the mixture, with stirring, during 3 hr; the mixture was then filtered and the precipitate washed with 95% ethanol and ether. The precipitate was resuspended in ethanol and ether several times and the combined extracts concentrated under reduced pressure. The residual oil was distilled in a small retort (bath temperature 130°) at 0.1 mm to yield 47.2 g. (83%) of 3,3-diethoxy-2-(hydroxymethyl)-1-propanol as a viscous oil; NMR ($D_2O$): δ4.72 (s, 2, OH), 4.65 (one-half of AB quartet, 1, J = 7 Hz, CH), 3.70 (d, J = 5 Hz, 4, $CH_2OH$), 3.2–4.0 (two quartets and one-half of AB quartet obscured by $CH_2OH$ doublet, 5, $CH_2$ of $C_2H_5$ and CH), 1.12 (t, J = 7 Hz, 6, $CH_3$).

EXAMPLE 4

Trimethylolmethane

A solution of 3,3-diethoxy-2-(Hydroxymethyl)-1-propanol, 1.78 g. (0.01 mole) in 50 ml of water was treated with N sulfuric acid to adjust the pH to 2.5. After standing at 25° for 1 hr the solution and 0.5 g. of 5% ruthenium-charcoal catalyst were shaken with hydrogen (50 psi, 25°) until hydrogen uptake ceased (one mole-equivalent, 2 hr.). The mixture was treated with barium hydroxide solution to adjust the pH to 7.0 and then filtered. Concentration of the filtrate to dryness gave 1.00 g. (98%) of trimethylolmethane, m.p. 60°–64°; sublimation gave 0.94 g. m.p. 66°–68° (94% recovery); recrystallization from acetone gave chunky prisms, m.p. 67°–68° (77% recovery); NMR ($D_2O$) δ 4.80 (s, 3, OH), 3.68 (d, J = 6 Hz, 6, $CH_2$), 1.90 (m, J = 6 Hz, 1, CH). (d, J = 6 Hz, 6, $CH_2$), 1.90 (m, J = 6 Hz, 1, CH).

Anal. Calcd. for $C_4H_{10}O_3$: C, 45.27; H, 9.50. Found: C, 45.17; H, 9.46.

The overall yield of pure, sublimed trimethylolmethane based on unrecovered diethyl malonate was 54%.

To prepare trimethylolmethane trinitrate from trimethylolmethane, one merely reacts the triol with nitric acid according to established procedures such as those established, for example, for the preparation of nitroglycerine from glycerine and nitric acid. The trimethylol compound is also useful in the preparation of other esters such as the tributyrate which are useful as plasticizers. Such esters may, of course, be produced by the well known reaction of an alcohol (the trimethylol) with an acid.

What is claimed:

1. A method for producing trimethylolmethane comprising the steps of:
    a. reacting diethyl malonate with ethyl orthoformate in the presence of zinc chloride catalyst to produce ethyl ethoxymethylenemalonate;
    b. reacting ethyl ethoxymethylenemalonate with sodium ethoxide to produce diethyl diethoxymethylmalonate;
    c. reacting diethyl diethoxymethylmalonate with lithium aluminum hydride to produce 3,3-diethoxy-2-(hydroxymethyl)-1-propanol; and
    d. forming an aqueous solution of 3,3-diethoxy-2-(hydroxymethyl-1-propanol, adjusting the pH of said solution to 2.5 to produce 2-formyl-1,3-propanediol, and adding hydrogen and ruthenium-charcoal catalyst to produce trimethylolmethane.

* * * * *